United States Patent [19]

Scates et al.

[11] Patent Number: 5,206,434
[45] Date of Patent: Apr. 27, 1993

[54] PURIFICATION PROCESS FOR METHYL ACETATE

[75] Inventors: Mark O. Scates, Pearland; Russell K. Gibbs, Jr., Houston; G. Paull Torrence, Corpus Christi, all of Tex.

[73] Assignee: Hoechst Celanese Corporation, Somerville, N.J.

[21] Appl. No.: 615,939

[22] Filed: Nov. 19, 1990

[51] Int. Cl.$^5$ .................. C07C 67/27; C07C 67/48
[52] U.S. Cl. .................. 562/891; 562/517; 560/248; 560/232
[58] Field of Search .................. 562/891, 517; 560/248

[56] References Cited

U.S. PATENT DOCUMENTS 1,963,968  6/1934  Burke et al. .................. 560/248
4,252,748  2/1981  Hoch et al. .................. 568/411

FOREIGN PATENT DOCUMENTS 0070180  1/1983  European Pat. Off. .......... 562/891

Primary Examiner—José G. Dees
Assistant Examiner—B. Frazier
Attorney, Agent, or Firm—Donald R. Cassady

[57] ABSTRACT

Esters such as methyl acetate which contain carbonyl impurities including aldehydes are purified by adding to the esters an amino compound which reacts with the carbonyls to form water soluble nitrogenous derivatives, separating an organic ester phase from an aqueous derivative phase, and distilling the ester phase to further remove heavier impurities. The formation of nitrile from the nitrogenous derivative is minimized by adding water to the distillation column or washing the aqueous bottoms from distillation with water to further remove the derivatives from any ester contained in the bottoms. The organic phase recovered from the bottoms can be recycled to the distillation to recover ester.

10 Claims, 1 Drawing Sheet

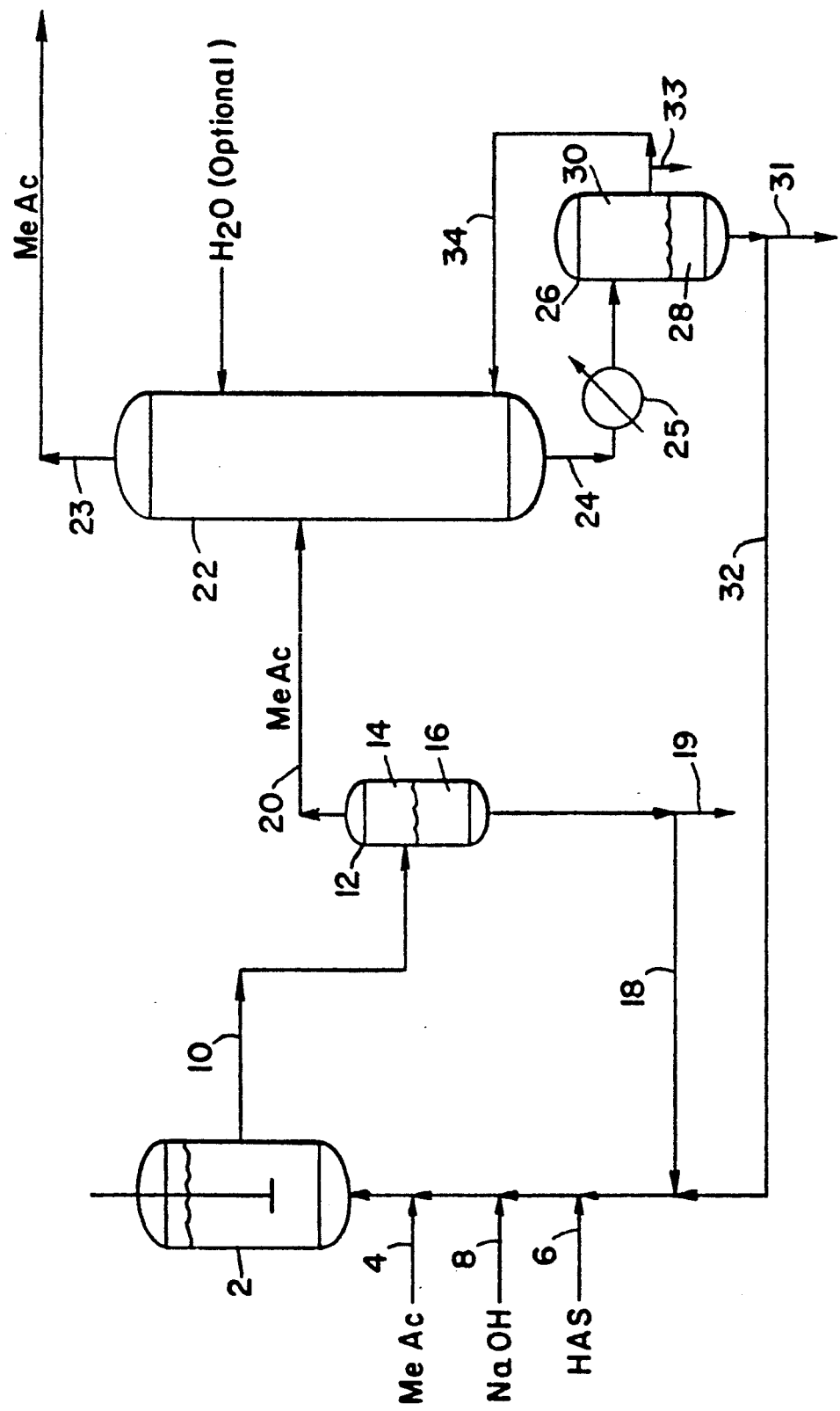

PURIFICATION PROCESS FOR METHYL ACETATE

BACKGROUND OF THE INVENTION

This invention relates to a process for purifying esters such as methyl acetate and, more particularly, the invention relates to a process for removing carbonyl impurities from such esters.

Methyl acetate is used as a feedstock in carbonylation processes such as to produce acetic anhydride or with methanol to coproduce acetic acid and acetic anhydride. It is also known to produce acetic acid only when methyl acetate is fed as a supplement or replacement feedstock for methanol in processes in which a stoichiometric amount of water is cofed with the methyl acetate. Unfortunately, methyl acetate made under certain esterification processes contains carbonyl impurities. For example, large volumes of impure methyl acetate are produced as a byproduct during the manufacture of polyvinyl alcohol from polyvinyl acetate. This impure methyl acetate has been recovered by a very expensive process in which the methyl acetate is converted to acetic acid by hydrolysis. In a typical process for producing polyvinyl alcohol, polyvinylacetate is reacted with methanol in the presence of a base to yield polyvinylalcohol and methyl acetate. This methyl acetate stream is contaminated with a variety of carbonyl components including acetaldehyde. Prior methods of recovering this methyl acetate stream have involved contacting the methyl acetate stream with an acid catalyst such as an acid resin in the presence of water which converts the methyl acetate to acetic acid and methanol which can be reused to convert the polyvinylacetate to polyvinylalcohol.

The presence of carbonyl impurities is very objectionable in many of the uses to which methyl acetate is put including carbonylation processes for the production of acetic acid or acetic anhydride or coproduction of these two materials. During the production of acetic acid by the carbonylation of methanol or methyl acetate and water, it has now been discovered by the present inventors that carbonyl impurities such as acetaldehyde, acetone, methyl ethyl ketone, crotonaldehyde, etc. react to form aldol condensation products and/or react with iodide catalyst promoters to form multicarbon alkyl iodides. If contained in the final acetic acid product, these impurities cause quality problems. In the production of acetic anhydride or in acetic acid/acetic anhydride coproduction by carbonylation of methyl acetate, it is known that undesirable high boiling tars are formed in the catalyst solution. The tars are believed to be formed by aldol condensation of the aldehydes and ketones as well as by reaction of the carbonyl and aldol products with the formed acetic anhydride. The tars bind with or otherwise entrap the Group VIII metal carbonylation catalyst and, upon precipitation from the catalyst solution, remove the catalyst. Thus, not only has the precipitated tar become an environmental problem, the operation of the commercial carbonylation process has been degraded and made more costly as make-up catalyst is required. In order to solve this problem, the prior art has treated the carbonylation catalyst recycle stream to remove undesirable components such as acetone or attempted to remove the metal carbonylation catalyst from high boiling residues. The treatment of the symptom is costly and not overly effective.

Unfortunately, it is difficult to remove the minor amounts of carbonyl impurities present in methyl acetate by conventional means such as distillation inasmuch as such impurities have boiling points close to that of methyl acetate.

Various processes have been suggested to remove the minute amounts of carbonyl impurities from esters. For example, it is known to remove aldehyde impurities from esters by contacting the ester with an amino compound, which amino compound reacts with the aldehydes. The reaction products are subsequently separated from the ester. An example of such a process is disclosed in U.S. Pat. No. 1,963,968 in which an ester such as methyl acetate is contacted with an amino compound such as aniline, phenylhydrazine, diphenylamine, hydroxylamine or ammonia, etc. The process involves vaporizing the ester and passing the amino compound in a liquid state or vaporizing the amino compound and passing same through the ester in a liquid state or contacting both the ester and amino compound in the liquid state in a reaction vessel and refluxing the liquids until the amino compound reacts with the aldehydes contained in the ester. The ester is recovered in a purified state by fractional distillation.

U.S. Pat. No. 3,290,363 discloses removing aldehydes from vinyl acetate by treating the vinyl acetate with an aromatic amine such as aniline and naphthylamines.

A similar process for the purification of acrylonitrile is disclosed in U.S. Pat. No. 2,770,644. In this process, acrylonitrile which contains minor amounts of methyl vinyl ketone is contacted with an aqueous solution of hydroxylamine hydrochloride, the mixture allowed to separate into two layers and the acrylonitrile separated from the reaction mixture. A pure acrylonitrile can be obtained by distillation.

While the removal of minute quantities of carbonyls from organic streams by a process which involves contacting the organic stream with amino compounds and subsequent separation by distillation has been successful in removing the carbonyl impurities, the process has several disadvantages. For one, typically large excesses of the amino compound relative to the amount of carbonyls present in the organic stream are utilized. Thus, material costs as well as energy costs involved in the separation stage such as by distillation of the organic stream from the reacted impurities are disadvantageous.

It has also been discovered by the present inventors that the product which is formed by the reaction of an aldehyde impurity and an amino compound can be converted to a nitrile during the distillation stage used to separate the reactants from the purified organic feed. Thus, acetaldehyde has been found to convert to acetonitrile by the prior art process. The formed nitriles do not easily separate along with the other impure reaction products and remain in the ester feed stream. The presence of nitriles such as acetonitrile in an ester stream is a great disadvantage in many processes including the carbonylation of methyl acetate to acetic anhydride or to the corresponding coproduction of acetic acid and acetic anhydride as described above. Also keto impurities may form undesirable nitrogenous derivatives upon reaction with the amino compound and subsequent heating during distillation. Such nitrogenous keto species may also be difficult to separate from like boiling product esters.

The prior art has not recognized the problem of nitrile formation during processes of removing carbonyls from ester streams by amino compound addition. Accordingly, there is a need to purify organic streams such as methyl acetate containing minor amounts of aldehydes without producing nitriles.

SUMMARY OF THE INVENTION

In accordance with the present invention, methyl acetate which contains carbonyl, including aldehyde impurities, is treated with an amino compound to convert the carbonyl impurities to water soluble nitrogenous derivatives and the methyl acetate is separated from the derivatives by a process which substantially eliminates the conversion of any reacted aldehyde to nitrile and the possible recontamination of the methyl acetate stream. The process is particularly useful in removing acetaldehyde from methyl acetate without conversion to acetonitrile. The process involves a series of steps in which the methyl acetate stream is contacted with an amino compound to convert the carbonyls to water soluble nitrogenous derivatives, phase separation of the methyl acetate stream from the aqueous derivative stream, distillation of the methyl acetate stream to remove remaining derivatives, and treatment of the bottoms stream from distillation with water to wash away or reduce derivative levels and minimize formation of nitriles. The distillate is a pure methyl acetate stream free from carbonyls and free from nitriles such as acetonitrile.

BRIEF DESCRIPTION OF THE DRAWING

The FIGURE is a schematic of the total methyl acetate purification process of the present invention.

DETAILED DESCRIPTION OF THE INVENTION

The methyl acetate stream which is to be purified in accordance with the process of the present invention can be any methyl acetate stream which contains carbonyl impurities including both ketone and aldehyde impurities. Acetaldehyde is a particularly troublesome impurity in view of the discovery that such impurity can be converted to acetonitrile by prior art amino treatment. While many processes for producing methyl acetate either as a primary product or as byproduct yield methyl acetate streams containing carbonyl impurities, a particular prevalent source of methyl acetate is obtained from the conversion of polyvinylacetate to polyvinylalcohol as described above.

While the present invention is particularly concerned with purifying methyl acetate, other esters can be purified using the process of this invention. Some of the common esters which may be purified by this process are as follows: methyl acetate, ethyl propionate, ethyl butyrate, ethyl valerate, propyl propionate, butyl propionate, butyl butyrate, propyl butyrate, propyl acetate, butyl acetate, amyl acetate, amyl propionate, and hexyl acetate.

In accordance with the process of the present invention, methyl acetate which contains carbonyl, including aldehyde, impurities is reacted with an aqueous solution of an amino compound to convert the carbonyl impurities to nitrogenous derivatives which are soluble in the aqueous phase. Subsequent to reaction, the methyl acetate is separated from the aqueous derivative phase in such a manner to provide a pure methyl acetate free from carbonyl impurities and to minimize any conversion of the nitrogenous aldehyde derivatives to nitriles which can contaminate the purified methyl acetate stream.

In the first stage of the process, the methyl acetate stream which contains carbonyl impurities including aldehyde is contacted with an aqueous amino compound solution, preferably an aqueous hydroxylamine salt, e.g., hydroxylamine hydrochloride, hydroxylamine sulfate, hydroxylamine bisulfate, or hydroxylamine phosphate. Since hydroxylamine slowly decomposes in its free form, it is commercially supplied as its acid salt. The free hydroxylamine is liberated upon treatment of the acid salt with a base such as potassium hydroxide, sodium hydroxide or lithium hydroxide. If sodium hydroxide is used as the base to liberate the hydroxylamine from its acidic sulfate salt, then such liberation also produces sodium sulfate as a byproduct.

The base should be used in an amount, for example, of 0.5 to 2 molar equivalents per molar equivalent of starting hydroxylamine. The base is preferably used in an amount of 0.8–1.0 molar equivalents per molar equivalent of starting hydroxylamine so that a small amount of hydroxylamine remains in the form of its acid salt to create a pH buffer that maintains the pH of the reactant solution in the range of 4.5 to 7. Use of larger amounts of base can cause the Ph to rise above 7 and result in initiating undesirable condensation reactions of methyl acetate and the free hydroxylamine which is formed, saponification of the methyl acetate and decomposition of the unstable hydroxylamine free base to undesirable volatile by-products such as ammonia. The hydroxylamine acid salt is preferably used in an amount of 1 to 2 molar equivalents of starting hydroxylamine per mole of the carbonyl impurities which are contained in the methyl acetate. The amount of carbonyl impurities can be determined by analytical methods prior to reaction. It is also important that the pH of the reaction solution does not fall below about 4.5 or the base will not free the hydroxylamine from its acid salt. The reaction is run at a temperature of about 0° to 70° C. for a period of from about 1 min. to 1 hour. Any pressure may be used and is not critical in the process.

Although hydroxylamine is the preferred amino compound for use in the process of this invention, other amino compounds are suitable including aniline and acid salts thereof such as aniline acetate, aniline sulphate, hydrazine, phenylhydrazine; alkyl amines such methylamine, ethylamine, propylamine, phenylamine, and naphthylamine.

Regardless of the type of amino compound used, nitrile formation from the reaction product of an aldehyde and amino compound can result during prolonged heating such as during distillation. Reaction of hydroxylamine and aldehydes yields an oxime whereas reaction with hydrazine yields the hydrazone. The nitrile forming reactions are shown below for (1) oxime products and (2) hydrazone products.

Subsequent to the addition of amino compound and reaction thereof with the carbonyl impurities, it is necessary to separate the methyl acetate from the nitrogenous products. In accordance with the present invention, a series of steps are utilized to provide this separation and yield a purified methyl acetate product and, in particular, a pure methyl acetate product which is free from nitrile. Unfortunately, typical distillation procedures which are used to separate purified organic streams from the nitrogenous products formed by reaction of the aldehyde impurities and the amino compound as in the prior art tend to produce nitriles by the reaction schemes described above upon prolonged heating.

The separation of the pure methyl acetate from the impure nitrogenous reaction product can be more readily described by referring to the Figure which is a schematic of the total methyl acetate purification process of the present invention. In the drawing and following example, hydroxylamine is used as the amino compound. It is to be understood that any ester feed and any reactive amino compound are useful in the process of this invention and, thus, the description below is not intended to limit the invention. Thus, referring to the Figure, it can be seen that entering reactor 2 is a methyl acetate feedstream 4, hydroxylamine sulfate feedstream 6, sodium hydroxide feedstream 8 and recycle aqueous phase 18. The reaction takes place in reactor 2 as described above in which the carbonyl impurities contained in the methyl acetate stream are reacted with hydroxylamine to form oximation products which are soluble in the aqueous phase. The reactor can be of any suitable equipment known in the art including a stirred back-mix or plug flow reactor.

Subsequent to reaction, the reaction products are collected via line 10 from reactor 2 and directed to decanter 12 for separation of the purified methyl acetate phase 14 from the aqueous phase 16 which contains unreacted hydroxylamine sulfate as well as most of the oximation products from reaction of the carbonyl impurities in the methyl acetate with the hydroxylamine. The aqueous phase containing the hydroxylamine sulfate is partially recycled to reactor 2 via line 18 and partially purged via line 19. The recirculation of the aqueous phase greatly improves pH control which is necessary to release the hydroxylamine from the hydroxylamine salt and allows reaction with the carbonyl impurities. Recirculation of the aqueous phase also minimizes usage of hydroxylamine. The organic phase 14 containing methyl acetate, minor amounts of water as well as trace amounts of hydroxylamine sulfate, oximes and impurities which do not separate with the aqueous hydroxylamine sulfate phase is withdrawn from the decanter 12 via line 20 and directed to distillation tower 22 for removal of these components from the methyl acetate. Upon distillation in tower 22, a distillate containing a purified methyl acetate stream leaves the tower via line 23. This light ends stream comprises methyl acetate and approximately 3 wt. % water. The bottoms 24 from distillation tower 22 comprises the separated aqueous oximes as well as other impurities such as alkanes, ethyl acetate and a small proportion of methyl acetate. The bottoms stream 24 is recycled to distillation tower 22 to recover any methyl acetate which leaves the bottom of the column in line 24.

However, it is important to reduce the oxime content of bottoms 24 which is recycled back to distillation tower 22. It has been discovered that oximes such as formed by reaction of the hydroxyl amine and aldehydes, in particular, acetaldehyde oxime can readily convert to the nitrile, e.g., acetonitrile, which has a boiling point close to methyl acetate and which will contaminate the methyl acetate distillate leaving distillation tower 22. Accordingly, in order to remove any oxime as well as nitrile from the bottoms 24 leaving distillation tower 22, the bottoms product is cooled via condenser 25 and directed to decanter 26 which separates the bottoms product into two phases, i.e., a heavy aqueous phase 28 containing oxime, dissolved acetate esters, sodium sulfate and, any unreacted hydroxylamine sulfate which remains in aqueous solution and a light organic phase 30. The aqueous heavy phase 28 is removed as effluent via line 31 or it can be partially recycled to reactor 2 via line 32. The light organic phase 30 is recycled to distillation column 22 via line 34 for further recovery of any methyl acetate contained in the bottom phase 24 or fully or partially purged from the column via line 33. To improve oxime removal from the methyl acetate, additional water can be added to the distillation tower 22 or to decanter 26 during phase separation. The decanter 26 further reduces the boiling point of bottoms 24 and, thus, allows for lower temperatures to be used during distillation. The lower temperature reduces nitrile formation during distillation.

Methyl acetate which is purified of carbonyl impurities is particularly useful as a feed for carbonylation processes for the formation of acetic acid and/or acetic acid and acetic anhydride coproduction. Thus, methyl acetate purified in accordance with the present invention does not contain nitrile impurities which can greatly degrade the acetic acid product. Moreover, a methyl acetate stream which is free from the aldehyde and ketone impurities will result in a substantial reduction in gums or tars which are typically formed in the acetic acid/acetic anhydride coproduction units and which as before said, entrap the catalyst and pull the Group VIII metal carbonylation catalyst from the catalyst solution. Thus, using a methyl acetate stream purified from carbonyl impurities can result in a substantial savings in catalyst which is needed to operate the carbonylation process and moreover, results in a less environmentally damaging byproduct.

The following examples are included for the purpose of illustrating the invention only and are not intended to limit the claimed scope of the invention strictly to the embodiments shown.

COMPARATIVE EXAMPLE

This example demonstrates the formation of acetonitrile which occurs when using conventional distillation techniques on a methyl acetate stream treated with aqueous hydroxylamine sulfate. A mixture consisting of
132 gm water
58 gm methyl acetate
0.35 gm acetaldehyde
1.00 gm methyl ethyl ketone
0.71 gm acetone
0.48 gm methyl isopropyl ketone
18 ml 30% hydroxylamine sulfate
5.5 ml 40% sodium hydroxide
was allowed to mix for 30 minutes and then subsequently distilled atmosphere pressure to obtain 20 grams of methyl acetate distillate product. The distillate was analyzed by gas chromatography and found to contain
<5 ppm acetone
20 ppm methyl ethyl ketone
<1 ppm methyl isopropyl ketone
8 ppm acetonitrile
The contamination of the product methyl acetate with acetonitrile was not expected and renders the product unsuitable for many uses since even low levels of nitrogenous compounds are frequently catalyst poisons in chemical processes or present other undesirable problems in various end uses.

EXAMPLE 1

A continuous process to purify impure methyl acetate as illustrated in FIG. 1 was used to purify a methyl acetate feed consisting of

| | |
|---|---|
| 4.1% | water |
| 203 ppm | ethyl acetate |
| 279 ppm | methyl ethyl ketone |
| 94 ppm | acetone |
| 95 ppm | acetaldehyde |
| 90 ppm | methyl isopropyl ketone |
| 2500 ppm | $C_8$–$C_{11}$ alkanes |

Operating conditions were:

| | |
|---|---|
| Column feed rate from feed decanter (20) | 18.95 gm/min |
| 30% aqueous hydroxylamine flow to reactor (6) | 0.201 gm/min |
| 30% sodium hydroxide flow to reactor (8) | 0.075 gm/min |
| Column aqueous residue purge (31) | 0.41 gm/min |
| Column base circulation rate to decanter (24) | 45 ml/min |
| Column organic residue purge (33) | 0.056 gm/min |
| Column reflux/distillate ratio | 1.0 |
| Aqueous purge from column feed decanter (19) | 0.22 gm/min |
| Column reflux temperature | 58.6 C |
| Column feed temperature | 22.0 C |
| Column base temperature | 63.0 C |
| 40 tray column (22) with feed (20 on tray 20 | |

The resulting distillate product (purified methyl acetate) was analyzed by gas chromatography and contained:

| | |
|---|---|
| 2.9% | water |
| 50 ppm | ethyl acetate |
| <10 ppm | methyl ethyl ketone |
| <10 ppm | acetone |
| <10 ppm | acetaldehyde |
| <10 ppm | methyl isopropyl ketone |
| 155 ppm | alkanes |

As can be seen, impurity removal is excellent and there is no formation of the undesirable acetonitrile using this process.

What is claimed is:

1. In a process for carbonylating methyl acetate to acetic anhydride, acetic acid or to coproduce acetic acid and acetic anhydride in the presence of a Group VIII metal carbonylation catalyst, the improvement which comprises: using as said methyl acetate a methyl acetate stream which contains carbonyl impurities and has been purified prior to carbonylation to remove said carbonyl impurities by contacting said methyl acetate with an aqueous solution of an amino compound under conditions at which said amino compound reacts with said carbonyl impurities for conversion to water soluble nitrogenous derivatives of said carbonyls, forming two separate phases comprising an organic phase containing a major portion of said methyl acetate and an aqueous phase containing said nitrogenous derivatives, distilling said organic phase and recovering a purified methyl acetate distillate stream for use in said carbonylation.

2. The process of claim 1 wherein said methyl acetate contains ketone impurities.

3. The process of claim 1 wherein said methyl acetate contains aldehyde impurities.

4. The process of claim 1 wherein said amino compound is hydroxyl amine.

5. The process of claim 1 wherein said distillation of said organic phase forms an aqueous bottom phase containing said nitrogenous derivatives, phase separating said aqueous bottom phase into an organic phase which contains methyl acetate and a residual aqueous phase which contains said nitrogenous derivatives and recycling at least a portion of said methyl acetate-containing organic phase to said distillation.

6. The process of claim 1 wherein additional water is added to said distillation to enhance removal of said nitrogenous derivatives from said ester distillate stream.

7. The process of claim 5 wherein water is added to said aqueous bottom phase to enhance removal of said nitrogenous derivatives from said organic phase which contains the ester.

8. The process of claim 5 wherein water is added to said distillation to enhance removal of said nitrogenous derivatives from said methyl acetate distillate stream and further adding water to said aqueous bottom phase to enhance removal of said nitrogenous derivatives from said organic phase which contains methyl acetate.

9. The process of claim 1 wherein said purified methyl acetate stream is carbonylated to acetic anhydride.

10. The process of claim 1 wherein said purified methyl acetate stream is carbonylated to co-produce acetic anhydride and acetic acid.

* * * * *